United States Patent [19]

Blaschke et al.

[11] Patent Number: 4,609,747
[45] Date of Patent: Sep. 2, 1986

[54] NOVEL WATER-SOLUBLE ANTIMONY COMPOUNDS AND THEIR PREPARATION

[75] Inventors: Marilyn W. Blaschke, Pearland; Richard F. Miller; John Link, both of Humble, all of Tex.

[73] Assignee: Atlantic Richfield, Los Angeles, Calif.

[21] Appl. No.: 672,555

[22] Filed: Nov. 19, 1984

[51] Int. Cl.$^4$ .............................................. C07F 9/90
[52] U.S. Cl. ........................................ 556/77; 556/76
[58] Field of Search ..................... 260/446; 556/76, 77

[56] References Cited

U.S. PATENT DOCUMENTS

| | | | |
|---|---|---|---|
| 3,728,367 | 4/1973 | Yates .................................... | 260/446 |
| 3,732,182 | 5/1973 | Chimura et al. ................. | 260/446 X |
| 3,752,837 | 8/1973 | Okuto et al. ........................ | 260/446 |
| 3,764,378 | 10/1973 | Kemp .............................. | 260/446 X |
| 3,888,774 | 6/1975 | Kemp .............................. | 260/446 X |
| 4,010,104 | 3/1977 | Radlmann et al. ............. | 260/446 X |
| 4,018,809 | 4/1977 | Radlmann et al. ................. | 260/446 |

Primary Examiner—Helen M. S. Sneed
Attorney, Agent, or Firm—Coleman R. Reap

[57] ABSTRACT

Novel organic water-soluble antimony compounds are prepared by reacting an alkoxyalkylamine with a hydroxycarboxylic acid to form an intermediate product and then reacting the intermediate product with an antimony oxide. These compounds are useful for use as catalyst metal poison passivators.

9 Claims, No Drawings

NOVEL WATER-SOLUBLE ANTIMONY COMPOUNDS AND THEIR PREPARATION

FIELD OF THE INVENTION

The present invention relates to novel water-soluble antimony compounds which are useful as hydrocarbon cracking catalyst metal poison passivators and to the preparation of these novel water-soluble antimony compounds.

RELATED CASE

U.S. application Ser. No. 672557, filed Nov. 19, 1984, relates to a method of passivating hydrocarbon cracking catalyst metal poisons using water-soluble antimony compounds.

BACKGROUND OF THE INVENTION

Silica-containing or silica-alumina-containing materials are conventionally employed in the catalytic cracking of hydrocarbons for the production of gasoline, motor fuel, blending components and light distillates. Such materials are frequently associated with zeolitic substances. These zeolitic substances can be naturally occurring, or they can be produced by conventional ion exchange methods to provide metallic ions which improve the activity of the catalyst.

While the presence of certain metals in the catalyst can be beneficial, the presence of others is detrimental. It is well known that varying amounts of metals such as nickel, copper, cobalt, vanadium and iron cause deterioration of the cracking catalyst during the cracking process. In fact, some oils contain these metals in such a high concentration that they cannot be economically cracked into gasoline and other fuels. The metals accumulate on the cracking catalyst and cause increased hydrogen production and coke laydown on the cracking catalyst, thereby adversely affecting the yield of desired products.

It has heretofore been proposed that in hydrocarbon cracking processes those deleterious metals contained in the hydrocarbon feedstock can be passivated by treating the cracking catalyst with compounds containing antimony, tin, indium or bismuth (see U.S. Pat. Nos. 4,238,362, 4,279,735 and 4,257,919). Antimony compounds are particularly useful as passivating agents and use of a wide variety of both organic and inorganic antimony compounds have been proposed for that purpose (see U.S. Pat. Nos. 4,111,845 and 4,153,536). Other organic antimony compounds proposed are various antimony tricarboxylates. These antimony compounds, for the most part, have been used in the form of a hydrocarbon solution. Some antimony compounds, such as antimony trioxide, have been used in the form of aqueous slurries or emulsions. It would be advantageous to have water-soluble antimony compounds that would not introduce additional cracking catalyst poisons available for use as cracking catalyst poison passivators. Such compounds could be easily and conveniently injected into catalytic cracking units. Water-soluble antimony salts could be prepared by neutralizing antimony carboxylates with alkali or alkaline earth metal compounds, such as oxides or hydroxides, but the alkali or alkaline earth metal would itself act as a poison to the cracking catalyst, thus defeating the purpose of using the antimony compound.

It is an object of the invention to present novel organoantimony compounds. It is another object of the invention to present novel water-soluble organoantimony compounds. It is another object of the invention to present novel water-soluble antimony compounds which have utility as cracking catalyst metal poison passivators. It is another object of the invention to present a process for preparing water-soluble antimony carboxylates which are free of cracking catalyst poisons. These and other objects of the invention are supported in the following description and examples.

SUMMARY OF THE INVENTION

Novel antimony compounds have now been discovered which have good water-solubility and which can be easily and efficiently introduced into a hydrocarbon catalytic cracking unit. These novel compounds are antimony amino carboxylic acid salts which are prepared by the reaction of an alkoxyalkylamine with a hydroxycarboxylic acid and the subsequent reaction of the resulting product with antimony oxide.

DETAILED DESCRIPTION OF THE INVENTION

Considering the invention in more detail, the novel products are prepared by (a) reacting a mono-, di- or trifunctional alkoxyalkylamine with a hydroxycontaining saturated aliphatic acid, (b) reacting the product of (a) with an antimony oxide, and (c) recovering the antimony salt.

The alkoxyalkylamines which may be used in the invention have the structural formula:

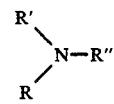

wherein R and R' may be identical or different and each may be hydrogen, a straight- or branch-chained alkyl group having 1 to 10 or more carbon atoms or a straight- or branch-chained alkoxyalkylamine group having 2 to 10 or more carbon atoms and R'' is a straight- or branch-chained alkoxyalkyl group having 2 to 10 or more carbon atoms. The term "alkoxyalkyl group" is used to designate a radical having the structural formula $R^3$—O—$R^4$ wherein $R^3$ is an alkyl group and $R^4$ is an alkylene group. The relative number of carbon atoms in $R^3$ and $R^4$ is not critical, subject to the above-stated limitation that the maximum number of carbon atoms in the alkoxyalkylamine is about 12.

When R, R' and R'' are alkyl groups they usually each have 1 to about 10 carbon atoms and preferably have 1 to about 6 carbon atoms and when they are alkoxyalkyl groups they usually have 2 to 10 and preferably have 3 to 6 carbon ations. R'' usually has 2 to about 10 and preferably has 3 to about 6 carbon atoms. The total number of carbon atoms in R, R' and R" is 2 to about 12 carbon atoms and preferably 3 to about 8 carbon atoms.

Typical alkoxyalkylamines include methoxymethylamine, methoxyethylamine, ethoxymethylamine, propoxymethylamine, butoxymethylamine, heptoxymethylamine, ethoxyethylamine, ethoxypropylamine, ethoxybutylamine, propoxypropylamine, propoxypentylamine, butoxybutylamine, butoxyhexylamine, butoxyoctylamine, 3-methylpentoxyethylamine, methoxy-2-ethylhexylamine, etc. The preferred alkoxyalkylamines are the lower alkoxyalkylamines, such as methoxymethylamine, methoxypropylamine, ethoxyethylamine, propoxymethylamine, etc.

The hydroxycarboxylic acids usable in the invention are those saturated, straight or branched aliphatic hydroxycarboxylic acids which react with alkoxyalkylamines and antimony oxide to form water-soluble products. Preferred hydroxycarboxylic acids are those which have a hydroxyl group in the alpha position, i.e. attached to the carbon atom which is adjacent to the carboxyl group. The hydroxycarboxylic acid may have more than one carboxyl group and more than one hydroxyl group. In general, although higher hydroxycarboxylic acids may be used, the preferred hydroxycarboxylic acids are those having 2 to about 10 total carbon atoms, 1 to about 4 carboxyl groups and 1 to about 4 hydroxyl groups, because these are commercially available and are economical to use.

Typical suitable hydroxycarboxylic acids include monohydroxy-monocarboxylic acids, such as hydroxyacetic acid (glycolic acid), alpha-hydroxypropionic acid (lactic acid), alpha-hydroxybutyric acid, alpha-hydroxy-alpha methylpentanoic acid, etc.; monohydroxypolycarboxylic acids, such as hydroxymalonic acid, hydroxysuccinic acid (malic acid), 2 hydroxy-1,2,3-propanetricarboxylic acid (citric acid), etc.; polyhydroxy-monocarboxylic, acids such as 2,3-dihydroxypropionic acid, 2,5-dihydroxypentanoic acid, 2,3,4 trihydroxybutyric acid, 2,3,4,5,6-pentahydroxyhexanoic acid (gluconic acid), etc.; and polyhydroxypolycarboxylic acids, such as 2,3-dihydroxysuccinic acid (tartaric acid) 2,3,4 trihydroxyglutaric acid, etc. Preferred hydroxycarboxylic acids are the lower hydroxycarboxylic acids, such as tartaric acid, 2,4-dihydroxyglutaric acid, lactic acid, citric acid, etc.

The antimony oxide may be any oxide of antimony, however the preferred antimony oxides are antimony trioxide and antimony pentoxide since these are more stable and commercially available.

Mixtures of different alkoxyalkylamines and/or different hydrocarboxylic acids may be used in the preparation of the product.

The products of the invention are prepared by reacting together the alkoxyalkylamine, the hydroxycarboxylic acid and the antimony oxide. The order of addition of reactants to the reaction is not critical, however it is usually more convenient to first combine the alkoxyalkylamine and the hydroxycarboxylic acid and then form the final product by reacting the antimony oxide with the intermediate product. Alternatively all three reactants may be simultaneously combined. If the alkoxyalkylamine and/or the hydroxycarboxylic acid are liquid in their natural state at the reaction conditions the reaction may be carried out without the use of a solvent or diluent. However, it is usually preferable to use an inert diluent or solvent as the reaction vehicle. Suitable solvents are those in which the hydrocarboxylic acid is soluble. In general, the hydroxycarboxylic acid is soluble in polar solvents, such as, water, alcohols, formamides, etc. The preferred solvent is water because it is inexpensive and does not introduce additional organic compounds into the units being treated.

The alkoxyalkylamine and hydroxycarboxylic acid reactants readily combine to form an intermediate salt product. This reaction usually occurs at ambient temperatures, although it is sometimes preferred to heat the reactants to increase the rate of dissolution of reactants and the rate of the reaction. In the case of the reaction between the intermediate salt and the antimony oxide, it's usually necessary to employ elevated temperatures. Any temperature less than the decomposition temperature of the products or reactants can be used. The reaction used in the manufacture of the final product is generally carried out at temperatures in the range of about 30 to 300° C. and preferably at temperatures in the range of about 50 to 200° C. The reactions of the invention can be carried out at any desired pressure.

The ratio of reactants is not critical and is usually determined by economics. If the reaction is carried out at reactant ratios other than stoichiometric it is preferred that the alkoxyalkylamine or the hydrocarboxylic acid be used in excess because antimony oxides are insoluble in water and are more expensive than the other reactants. Of course, the stoichiometric ratio of the reactants will vary depending upon the products formed. When polyfunctional carboxylic acids are used it is possible that more than one chemical compound will be formed. In general, about 1 to 10 and preferably about 2 to 6 moles of alkoxyalkylamine and about 1 to 10 and preferably about 2 to 6 moles of hydroxycarboxylic acid are used for each mole of antimony oxide.

In a typical procedure for preparing the products of the invention the selected alkoxyalkylamine is combined with an aqueous solution of the selected hydroxycarboxylic acid and the mixture is stirred, with or without heating, until a clear solution is formed. The antimony oxide is then added to the alkoxyalkylamine-hydroxycarboxylic acid solution and this mixture is heated with continuous agita-tion until all of the antimony oxide is dissolved, thereby forming the end product. The product may be used as is or it may be dried and used as a solid product.

Other substances, such as other cracking catalyst metal poison passivators or corrosion inhibitors may be added to the finished product, if desired.

The following examples illustrate specific embodiments of the invention. Unless otherwise specified, parts and percentages are on a weight basis EXAMPLE 1: Reaction of Tartaric Acid, Antimony Trioxide and Methoxyethylamine To a clean reaction flask was charged 23 gm. of distilled water, 16.6 gm. (0.11 mole) of tartaric acid, and 8.25 gm. (0.11 mole) of methoxyethylamine. An exothermic reaction took place and the mixture cleared to a colorless liquid. While the solution was mixing, 15 gm. (0.05 mole) antimony trioxide was added. This caused the solution to have a milky white appearance. The mixture was heated to reflux and held at that temperature for 26 hours The final product was a yellow liquid which was readily soluble in water.

EXAMPLE 2: Reaction of Tartaric Acid, Antimony Trioxide and Methoxypropylamine

The procedure of Example 2 was repeated except that 9.79 (0.11 mole) of methoxypropylamine was substituted for the methoxyethylamine. The final product was a yellow liquid which was readily soluble in water.

The foregoing examples illustrate embodiments of the invention, the examples showed that products which are readily soluble in water were obtained.

Although the invention has been described with reference to a specific example, it is understood that variations are comtemplated. The scope of the invention is limited only by the breadth of the appended claims.

What is claimed is:

1. A method of preparing water-soluble antimony compounds comprising:
   (a) reacting an alkoxyalkylamine with a hydroxycarboxylic acid and
   (b) reacting the product of (a) with an antimony oxide 2. A method of preparing water-soluble compounds of antimony comprising:
   (a) reacting (1) a nitrogen-containing compound having the structure

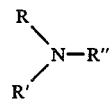

wherein R and R' are each independently hydrogen, an alkyl group having 1 to 10 carbon atoms or an alkoxyalkyl group having 1 to 10 carbon atoms and R" is an alkoxyalkyl group having 1 to 10 carbon atoms and the total number of carbon atoms in R, R' and R" is 1 to about 12, with (2) a hydroxycarboxylic acid having up to 12 total carbon atoms and containing 1 to 4 carboxyl groups and 1 to 4 hydroxyl groups, and wherein at least one of said hydroxyl groups is in the alpha position relative to a carboxyl group, and
   (b) reacting the product obtained in step (a) with an antimony oxide selected from antimony trioxide, antimony pentoxide and mixtures of these.

3. The process of claim 2 wherein R and R' each have 0 to about 4 carbon atoms R" has 2 to 4 carbon atoms and the total number of carbon atoms in R, R' and R" is 2 to about 10.

4. The process of claim 2 wherein the hydroxycarboxylic acid contains 1 to 4 carboxyl groups, 1 to 4 hydroxyl groups and a maximum of about 8 carbon atoms.

5. The process of claim 4 wherein the hydroxycarboxylic acid is selected from glycolic acid, tartaric acid, citric acid, lactic acid, malic acid and mixtures of these.

6. The process of claim 4 wherein the alkoxyalkylamine has 2 to about 6 carbon atoms.

7. The process of claim 6 wherein the alkoxyalkylamine is selected from methoxymethylamine, methoxyethylamine, methoxypropylamine, ethoxyethylamine, ethoxypropylamine, propoxyethylamine, propoxypropylamine and mixtures of these.

8. The process of claim 7 wherein the antimony oxide is antimony trioxide

9. A product prepared by the process of any one of claims 2 to 8.

UNITED STATES PATENT AND TRADEMARK OFFICE
CERTIFICATE OF CORRECTION

PATENT NO. :   4,609,747
DATED      :   September 2, 1986
INVENTOR(S) :  Blaschke, et al.

It is certified that error appears in the above-identified patent and that said Letters Patent is hereby corrected as shown below:

Amend claim 1 by inserting at Col. 5, line 40, after the word "oxide" the words --at an elevated temperature.--

Amend claim 2 by inserting at Col. 6, line 20, after the word "these" the words --at a temperature in the range of about 30 to 300°C.--

Signed and Sealed this

Third Day of March, 1987

Attest:

DONALD J. QUIGG

Attesting Officer

Commissioner of Patents and Trademarks